United States Patent [19]

Blechman et al.

[11] Patent Number: 4,595,361

[45] Date of Patent: Jun. 17, 1986

[54] MAGNETIC FORCE ORTHODONTIC KIT AND APPLIANCES CONSTRUCTED THEREFROM

[75] Inventors: Abraham Blechman, Tappan, N.Y.; Eugene A. Pescatore, Elmwood Park, N.J.

[73] Assignee: Medical Magnetics, Inc., Ramsey, N.J.

[21] Appl. No.: 693,268

[22] Filed: Jan. 22, 1985

[51] Int. Cl.$^4$ .............................................. A61C 3/00
[52] U.S. Cl. ........................................ 433/18; 433/19
[58] Field of Search ..................... 433/18, 19, 20, 22, 433/17, 8

[56] References Cited

U.S. PATENT DOCUMENTS

| | | | |
|---|---|---|---|
| 1,938,428 | 12/1933 | Johnson | 433/20 |
| 3,158,934 | 12/1964 | Waldman | 433/22 |
| 3,353,271 | 11/1967 | Blechman | 433/18 |
| 3,775,850 | 12/1973 | Northcutt | 433/20 |
| 4,424,030 | 1/1984 | Smiley et al. | 433/18 |
| 4,457,707 | 7/1984 | Smiley et al. | 433/18 |

FOREIGN PATENT DOCUMENTS 220858 7/1942 Switzerland ........................ 433/20

Primary Examiner—John J. Wilson
Attorney, Agent, or Firm—Hopgood, Calimafde, Kalil, Blaustein & Judlowe

[57] ABSTRACT

A kit is provided containing magnetic modules, attachment wire and a set of gages. The modules are rectangular prismatic formed from a cobalt-samarium alloy, covered with a chlorinated poly-p-xylene coating or stainless steel and jacketed in stainless steel with orthogonally related passages on opposite sides having rectangular cross-sections for receiving with a snug fit the rectangular cross-section attachment wire formed by welding together two lengths of standard edgewise wire. The gages provide means for spacing the modules when the latter are incorporated in an appliance.

Appliances are illustrated for accomplishing a variety of orthodontic procedures. The construction of the modules and attachment wire permits construction of appliances where the modules are constrained in the jaw closed in centric condition to translate parallel to their respective pole faces in a "sliding" fashion.

22 Claims, 11 Drawing Figures

MAGNETIC FORCE ORTHODONTIC KIT AND APPLIANCES CONSTRUCTED THEREFROM

BACKGROUND OF THE INVENTION

The present invention relates to the field of orthodontics and, more particularly, to the construction of magnetic force orthodontic appliances and to a kit therefor.

In U.S. Pat. No. 3,353,271, of Abraham Blechman, entitled "Magnetic Orthodontic Appliance" there is described an orthodontic appliance through which corrective traction is applied to teeth by magnetically generated force derived from permanent magnets mounted intraorally by arch wires and anchoring bands on the buccal sides of the teeth, the spacing between the magnets being adjusted to regulate the traction force produced. Three embodiments of magnets are described in the patent, the first is right rectangular prismatic of "Alnico", approximately 6 mm×4 mm×3 mm, and provided with a "Russel" lock at its small end to suspend it from a base arch wire. The magnetic polarization is across the 4 mm dimension between the 3 mm×6 mm faces. The second embodiment replaces the "Russel" lock with a groove for the arch wire and a setscrew to secure the element to the wire. Finally, the third embodiment has a right circular cylindrical magnet body with a buccal tube attached to one of the circular ends of the body.

While the Blechman patented appliance represented a significant advance in the art at the time, the magnets were bulky and provided limited versatility in construction of appliances from patient to patient.

In U.S. Pat. No. 4,424,030, of Harry Smiley and Abraham Blechman, entitled "Integrated Oral Magnetic Osteogenic and Orthodontic Appliances" there is described, inter alia, a magnetic module consisting of a permanent magnet anchored in a sleeve of surgical grade stainless steel by a bio-compatible adhesive material, such as an acrylic, epoxy, urethane, or other suitable material. The patent states that the exposed poles of the magnet are preferably coated with the adhesive material to prevent corrosion products from leaching into the oral cavity when SmCo or AlNiCo magnets are used. Mounting of the module is obtained in one embodiment by soldering to the lingual aspect of the module sleeve a rectangular orthodontic tube for mounting on 0.022"×0.028" arch wire.

Again, attaching conventional orthodontic tubes to the magnetic module produced a bulky component. Moreover, it has been discovered that the use of conventional arch wire for mounting the modules does not provide in a simple and convenient manner adequate rigidity to firmly mount a module in an appliance. Positive mounting of each module is necessary if predictable forces are to be obtained. Also, it was found that the single edgewise wire had a tendency to break.

Therefore, an object of the present invention is to provide magnetic modules, as part of an overall system for creating fixed appliances within the oral cavity, which modules are of significantly smaller size than those disclosed in said patents.

Another object is to provide such magnetic modules of smaller size without sacrifice of available traction forces.

A further object is to provide magnetic modules for construction of orthodontic fixed appliances, which modules are constructed in a manner that facilitates appliance construction and custom tailoring to the individual patient.

Yet another object is to provide magnetic modules that can be installed either buccally or lingually or both depending upon the desired orthodontic procedure, all without undue patient discomfort.

It is a further object of the invention to provide from commonly available orthodontic edgewise wire an attachment wire of increased strength and utility especially suited to mounting magnetic modules as comtemplated herein.

SUMMARY OF THE INVENTION

In accordance with one aspect of the present invention there is provided a module for use in construction of magnetic force orthodontic appliances in which the module is threaded on an attachment wire having a non-circular cross-section, said module comprising a body of permanently magnetized material and means defining at least two orthogonally related through passages of non-circular cross-section for receiving said attachment wire while precluding rotation of said module about said wire.

In accordance with another aspect of the present invention there is provided a universal kit for construction of said magnetic force orthodontic appliances comprising, in combination with a plurality of said modules, a supply of said attachment wire. Preferably, the attachment wire consists of two lengths of edgewise wire bonded together side-by-side. The kit, preferably, also includes a set of gages for use in spacing the modules during installation.

In accordance with a further aspect of the present invention there is provided a magnetic force orthodontic appliance in which permanent magnet modules are supported on attachment wires within the oral cavity coupled to teeth of the maxillary and mandibular arches for exerting a selected force in a predetermined manner for accomplishing a desired orthodontic procedure, comprising in combination supported on attachment wires at least three such modules each having a planar pole face of a given polarity, two of said modules being mounted in side-by-side relationship on one dental arch with their respective pole faces lying in a common plane, and the third module being mounted on the other dental arch on the opposite side of said plane from said first two modules spaced from said plane in the direction normal thereto by a predetermined gap and with its pole face parallel to said plane, said three modules being magnetically polarized and located relative to each other such that magnetic forces are exerted between said third module and said two other modules tending to translate said third module by a combination of attraction and repulsion to and from one and the other, respectively, of said first two modules, and means preventing said modules from closing said gap thereby constraining said modules to translate laterally relative to each other.

BRIEF DESCRIPTION OF THE DRAWINGS

The invention will be better understood after reading the following detailed description of the presently preferred embodiments thereof with reference to the appended drawings in which.

The same reference numerals are used throughout the drawings to designate the same or similar parts.

DETAILED DESCRIPTION OF THE PRESENTLY PREFERRED EMBODIMENTS

Figure 1:
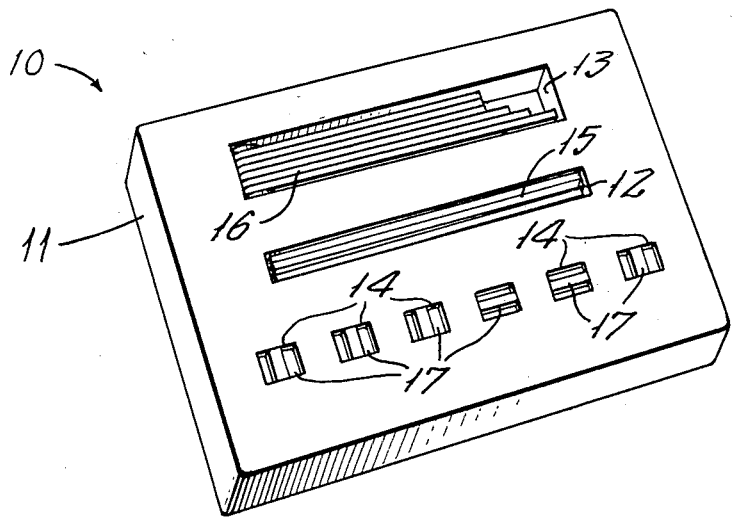
FIG. 1 is a perspective view of a typical kit package arrangement of magnetic modules, attachment wires and gages, embodying the present invention.

Referring to FIG. 1, there is illustrated an example of a package subassembly 10 holding the components that constitute a universal kit embodying the present invention. The subassembly 10, as shown herein, consists of a pallet 11 of foamed plastic or other suitable material with cutouts or recesses at 12, 13 and 14, for holding, respectively, a supply of attachment wire 15, a set of gages 16, and a supply of magnetic modules 17. The subassembly 10 can be enclosed within a suitable box (not shown) or can be sealed in plastic, or otherwise packaged, as desired. A simple snap-locked hinged plastic container (not shown) is presently preferred. If desired, the kit can be furnished with other parts such as a supply of conventional crimpable stops, the purpose of which will be apparent after the discussion to follow.

Figure 2:
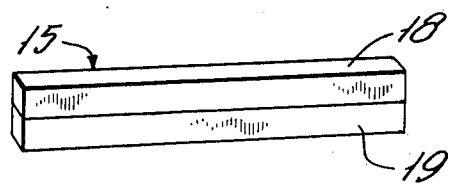
FIG. 2 is a perspective view of a length of attachment wire, included in the kit of FIG. 1, formed by joining lengths of edgewise wire along one side.

A typical length of attachment wire 15 is shown in FIG. 2. The wire 15 is constructed from standard edgewise wire segments 18 and 19 having cross-sectional dimensions of 0.022"×0.028". The segments 18 and 19 are joined by tack welding or the like with their narrow sides in contact to produce a wire with the cross-dimensions of 0.022"×0.056". For the present kit, it is preferred to supply the wires 15 in lengths of about 2.25". The welding of the individual segments 18 and 19 should be such as to resist fracture as the wire 15 is bent during appliance construction, but to permit separation or splaying of the segments where such is desired. For certain purposes, as will be explained below, it becomes desirable to remove a portion of one segment of the wire in order to convert from double wire to single wire. This is facilitated if the welding is at spaced intervals. By joining together commonly available edgewise wire to produce the attachment wire 15 it has been possible to obtain the necessary strength without undo expense, at the same time obtaining a construction versatility that would not be available with a monolithic wire. Specifically, it has been found extremely useful when constructing an appliance to be able to truncate one of the wire segments while using the extending portion of the other segment to establish a hook or the like. This reduces the appliance bulk and discomfort factor where the double wire strength is not needed.

It should be noted that the 0.022"×0.028" edgewise wire has heretofore always been installed with its long transverse dimension horizontal. It was this mode of installation that was contemplated in said Smiley et al. patent. All edgewise brackets have their slots designed for this orientation. Contrary to such common usage, the attachment wire 15 is intended to be used with its long transverse dimension vertical. In fact, both edgewise wire segments 18 and 19 are oriented in that same manner. From a strength standpoint, the wire 15 can be likened to an I-beam providing considerable bending resistance in the plane common to the two segments 18 and 19.

Figure 3:
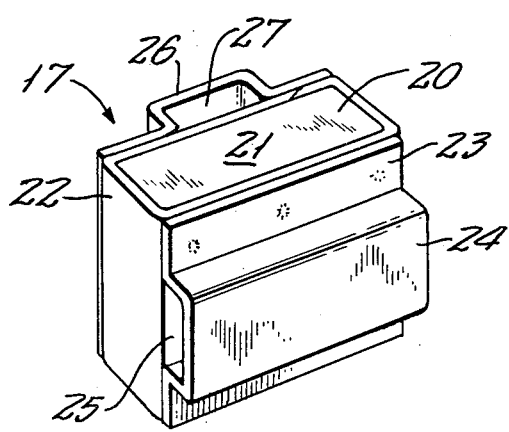
FIG. 3 is a perspective view of one embodiment of a magnetic module in accordance with the invention that can be included in the kit of FIG. 1.

Referring to FIG. 3, there is shown, drawn to a greatly enlarged scale, a single module 17. The module 17 consists of a parallelepiped shaped body 20, here a right rectangular prism, of a magnetized cobalt-rare earth alloy having an axis of magnetic polarization that extends between and normal to two opposing faces of said body, only one of which, face 21, is visible in the drawing. The body 20, although not apparent from the drawing, is covered on all surfaces with a coating layer of a bio-compatible material. At present, it is preferred to use Parylene-C, manufactured by Union Carbide Corporation, a coating composition of poly-p-xylene with a single chlorine atom replacing a hydrogen atom. Alternatively, the magnet alloy body 20 can be covered with a coating layer of a suitable stainless steel such as type 316L, applied by sputtering, a steel having the general percentage composition of 0.03 C; 2.00 Mn; 1.00 Si; 16.0–18.0 Cr; 10.0–14.0 Ni; 0.045 P; 0.03 S; 2.0–3.0 Mo; and the balance iron.

Over the coated magnet body 20 is assembled a jacketing sleeve 22 of stainless steel, preferably type 316L. To one side of the jacket 22 there is secured, by tack welds or the like, a stamping 23 of type 316L stainless steel having a raised portion or tunnel 24 defining a through passage 25 of generally rectangular cross-section, the dimensions of which conform closely to that of the wire 15. At present, it is preferred to provide a passage 25 having a cross-section about 0.022"×0.056". The precise dimensions should be selected to permit the wire 15 to be threaded through passage 25 without too much difficulty while developing a snug fit. If desired, the tunnel 24 can be crimped for immobilizing the module on the wire. Additionally, standard crimpable split round arch stops having an internal diameter of 0.051" and a length of 2 mm can be applied to the wire 15 on either side of the module 17 to further lock the module in position.

On the other side of the jacketing sleeve 22 another tunnel 26, formed similar to the tunnel 24, is secured, but with the longitudinal axis of the passage 27 through tunnel 26 being oriented orthogonally to the axis of passage 25. The cross-sectional shape and dimensions of passage 27 should be substantially the same as that of passage 25.

To summarize, it should be apparent that the tunnel 26 represents a tubular structure disposed with the longitudinal axis of its contained passage oriented parallel to the axis of polarization of the body 20 of magnetized material, while tunnel 24 represents a second tubular structure disposed on the opposite side of module 17 from the first mentioned tubular structure 26, the tubular structure 24 defining the through passage 25 of non-circular cross-section having a longitudinal axis located orthogonally with respect to said first through passage.

The drawing in FIG. 3 is greatly enlarged. Actually, the magnetic module is extremely small, smaller than the magnets described in the aforesaid patents. At present the pole face 21 is 2 mm×5 mm while the inter-pole distance is 4 mm. Taking the tunnel heights into consideration and the thickness of the sheet stock, the total thickness of the module in FIG. 3 is about 3.25 mm.

Cobalt-samarium alloy has been used to construct satisfactory modules as shown in FIG. 3. However, any other magnetic material having comparable magnetic force and coercivity characteristics can be used.

Figure 4:
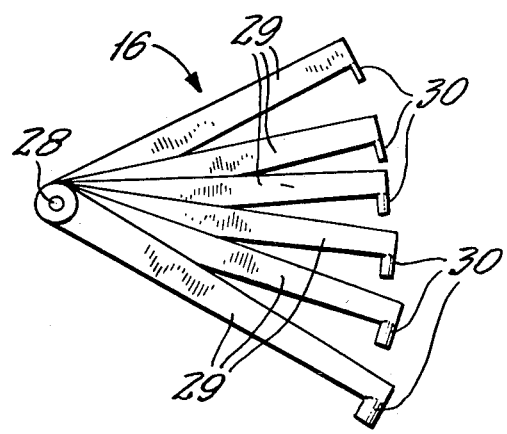
FIG. 4 is a top view of the gages included in the kit of FIG. 1.

Completing the kit is the gage set 16 shown in FIG. 4. The set of gages can be constructed of clear polycarbonate material fastened together by a suitable rivet 28. Each of six gage members has an arm 29 terminating in a circular cylindrical accurately dimensioned finger 30. At present the diameters of the fingers 30 are, respectively, 0.5 mm, 1.0 mm, 1.5 mm, 2.0 mm, 2.5 mm and 3.0 mm.

Referring to FIGS. 5 to 9, there are illustrated a number of exemplary fixed appliances that can be constructed using in combination the kit previously described and standard orthodontic devices such as bands, tubes, base arch wires, arch wire brackets and so forth. When considering the several examples it should be borne in mind that the magnetic modules can be combined in various combinations relying on the attraction between unlike poles or repulsion between like poles. Because each module 17 has two orthogonally related attachment wire receiving passages, the modules can be oriented conveniently with either pole face positioned to cooperate with an adjacent magnet.

Figure 5:
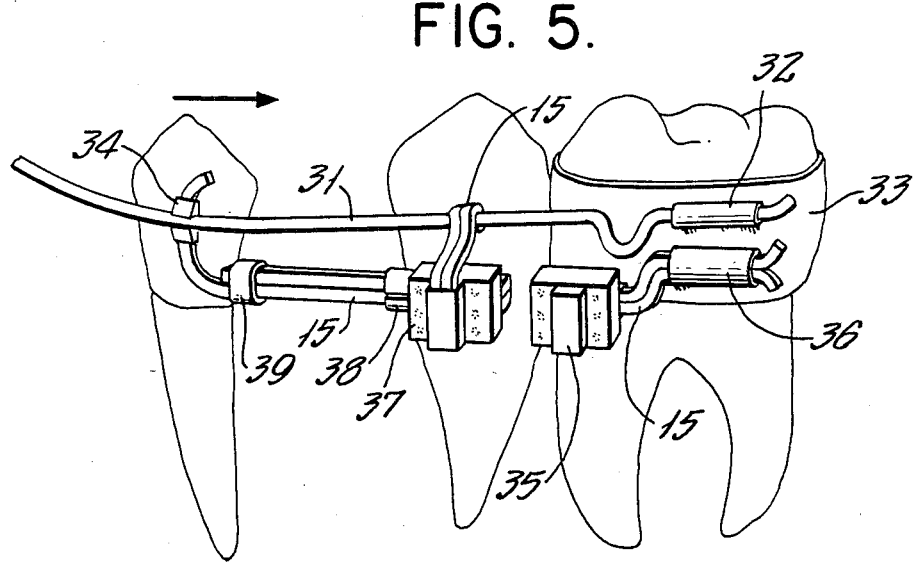
FIG. 5 is an elevational view illustrating an appliance constructed with the aid of the kit of FIG. 1, which appliance employs intramaxillary anchorage for translating a cuspid distally.

Considering FIG. 5, a standard base arch wire 31 is anchored via a tube 32 and a metal band 33 to a molar and strung around the lower dental arch (the appliance can just as effectively be applied to the upper dental arch) engaging in suitable brackets 34, one of which is shown bonded to the cuspid. To anchor the stationary magnet module 35, the module is fastened to a length of the special double edgewise attachment wire 15, the free end of which is secured in a standard Begg oval tube 36 mounted on band 33. A Begg tube having internal dimensions of 0.024"×0.072 " is utilized. If necessary, ligature wires or the crimpable stops should be added to secure the attachment wire to the tube 36.

For the illustrated procedure the magnetic modules should be oriented to attract. The second module, 37, is shown supported by two lengths of attachment wire 15, one extending vertically and looped over the base arch wire to form an eye translatable therealong. The other attachment wire is installed with stops 38 and 39 and with only one of its segments inserted through the conventional vertical slot in bracket 34. The other segment is truncated just beyond stop 39.

In this appliance the magnetic polarization axes are disposed horizontally and a gap is provided between confronting pole faces. With cobalt-samarium magnets dimensioned as described above, the breakaway force is about 290 gm (10.2 oz). Depending upon the size of gap, however, the force between the modules can be adjusted from 155 gm at a gap of 0.5 mm to 10 gm at 5.0 mm with the variation inbetween following an approximate square law. As shown, the appliance is intended to impart distal translation to the cuspid.

Figure 6:
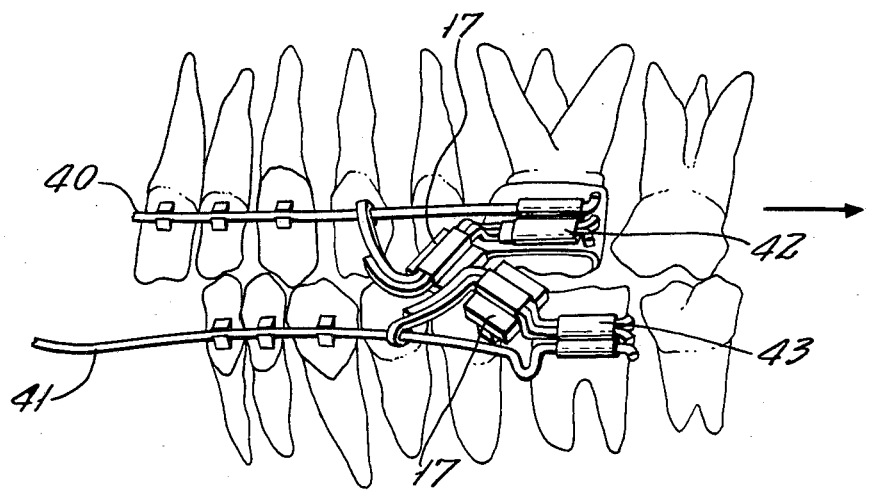
FIG. 6 is an elevational view illustrating an intermaxillary appliance for correcting a Class II malocclusion that can be constructed with use of the kit of FIG. 1.

FIG. 6 illustrates an intermaxillary appliance with the magnets in attraction. Here, base arch wires 40 and 41 are installed in conventional manner on the upper and lower arches anchored to the first molars. Using the Begg oval tubes 42 and 43 and attachment wires bent V-shape, the modules are secured to the respective arches for drawing distally a segment of the upper arch. The angled position of the modules provides sufficient tolerance for mandibular movement without interference.

Figure 7:
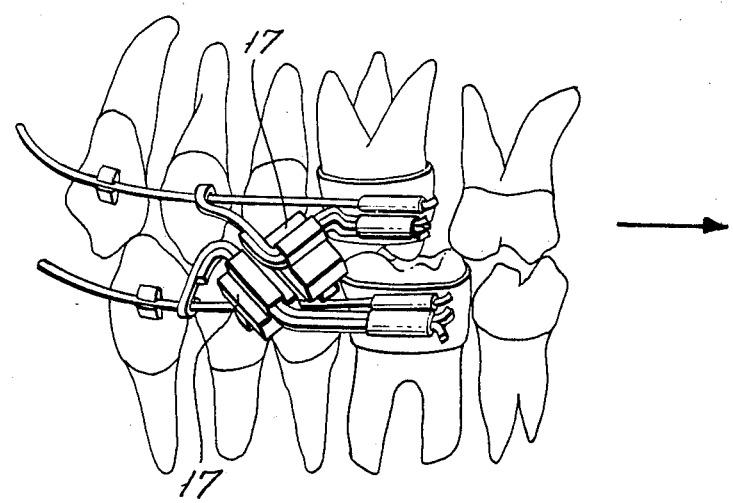
FIG. 7 is an elevational view illustrating an intermaxillary appliance for distalizing upper buccal segments.

FIG. 7 illustrates a reversal of the magnets over that used in FIG. 6. In FIG. 7 the magnets are acting in repulsion. Also because of the natural arc of mandibular motion, the modules can be arranged, if desired, to contact upon forcible closure of the jaw and thus contribute mechanically to the intended relative movement.

Frequently, the Orthodontist desires to accomplish without too frequent readjust of the appliance greater movement of the teeth than that provided with the appliances described above. For this purpose resort can be had to the principles underlying the appliance construction shown in FIGS. 8 and 9. For convenience, the relative motion between modules can be thought of as involving "sliding" motion although the relatively moving magnets are not actually in physical contact. Thus, in FIG. 8, modules 50 and 51 are mounted, each with vertical polarization, respectively on the upper and lower dental arches. If unlike poles are facing each other, because of the horizontal offset of module 50 mesially and module 51 distally, the attractive force will have a vector parallel to the occlusal plane tending to move the segments in the directions of the respective arrows 52 and 53. With a vertical separation of 0.01 mm when the jaws are closed in centric relation, attractive forces ranging from 35 gm with 0.5 mm horizontal offset to 70 gm with 3.0 mm horizontal offset is easily obtained. The maximum available force falls off to 50 gm with a vertical separation of 0.5 mm and drops to 35 gm at 1.0 mm separation. However, it can be shown that a much more stable force is obtainable over a horizontal movement of about 2 mm, then can be obtained when relying on movement normal to the magnetic pole faces. Also, when positioned one over the other, controlled vertical forces are available to correct bite opening, if desired.

Figure 8:
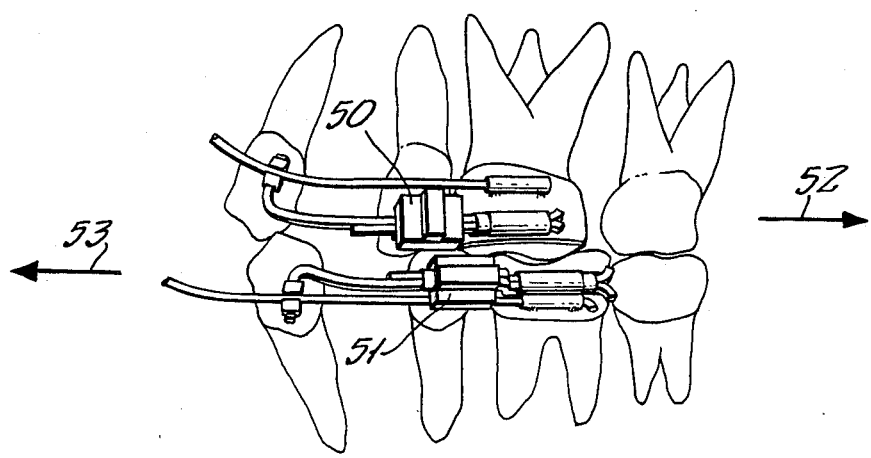
FIG. 8 is an elevational view illustrating the use of two magnet modules in "sliding" relationship providing intermaxillary force for accomplishing Class II mechanics.

Summarizing, it will be seen from FIG. 8 that the two modules 50 and 51 each has a planar pole face of a given polarity confronting the pole face of the other substantially in parallel and with a predetermined gap between the pole faces in the direction normal to the surfaces of said pole faces. The respective axis of magnetic polarization of each of modules 50 and 51 is offset laterally from a co-linear relationship such that there is developed between said modules a magnetic force having at least a vector component in a direction parallel to said pole faces. The mounting of the magnets in the appliance is such as to prevent the modules from totally closing the gap therebetween as the jaw is closed thereby preventing frictional binding.

The movement assumed for the appliance of FIG. 8 is based on confrontation of unlike pole faces. However, reverse forces can be developed by having like polarity poles facing each other. This arrangement can be useful in correcting anterior open bite and cross-bite problems.

Once the polarization axes depart from co-linearity, the separating force will have a vector component parallel to the confronting pole faces. This vector will tend to "slide" the modules either into or out of co-linearity depending upon whether the magnets are in attraction or repulsion.

Figure 9:
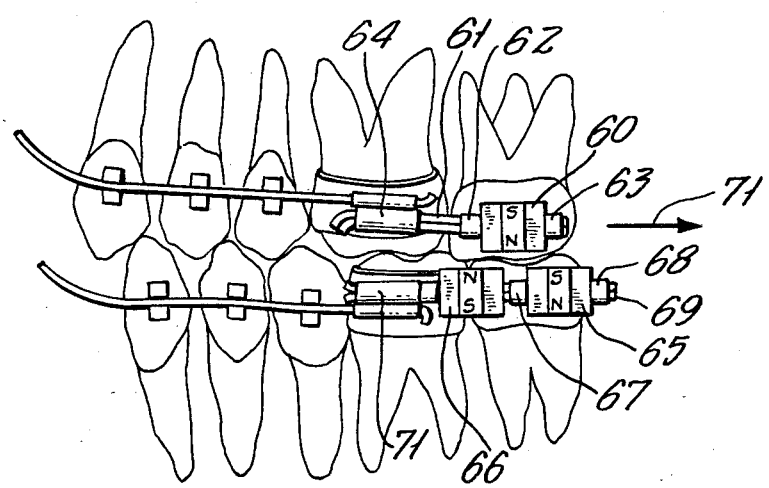
FIG. 9 is an elevational view illustrating the use of three magnetic modules in "sliding" relationship for accomplishing Class II mechanics where increased force and travel is required over that available from two modules.
Figure 10:
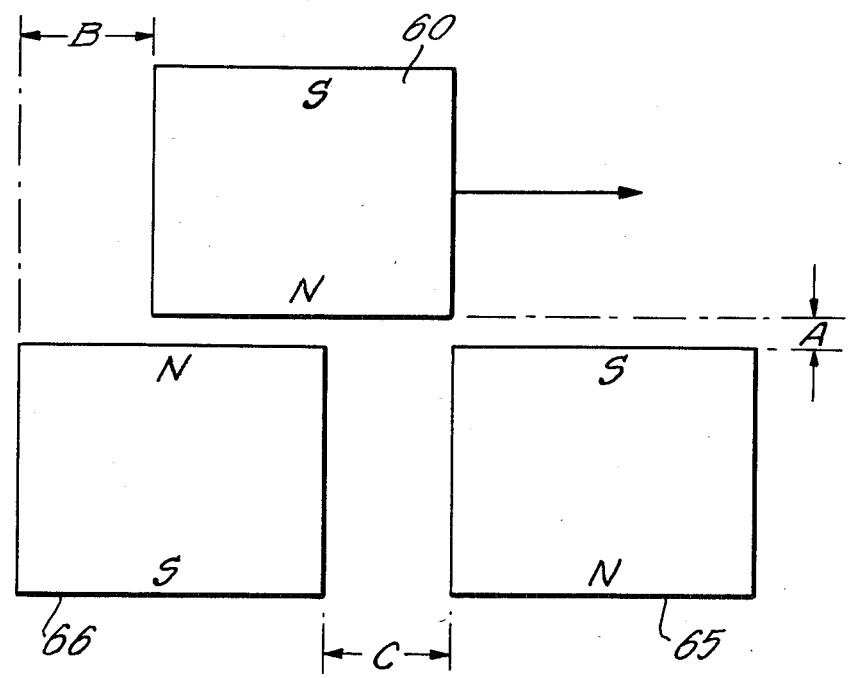
FIG. 10 is a diagrammatic view of three magnetic modules useful in explaining the basis of force determination in constructing an appliance of the type shown in FIG. 9.

The "sliding" principle can readily be extended to obtain increased forces and longer travel by adding modules as shown in FIG. 9 and illustrated diagrammatically in FIG. 10. In the example of FIG. 9, a module 60, polarized as shown, is mounted on attachment wire 61, between crimped stops 62 and 63. The wire 61 is secured in the Begg oval tube 64 secured to the upper first molar by a suitable band. Confronting module 60 are modules 65 and 66 located by crimped stops 67 and 68 on attachment wire 69 secured in Begg oval tube 70. The modules 65 and 66 are poled as shown.

Referring to FIG. 10, the diagram shows the significant dimensions, A designating the pole face gap, B designating the offset dimension arbitrarily referenced to the mesial surface of the module 66, and C designating the separation between the two modules 65 and 66 that are located on the same arch. With modules constructed and dimensioned as described above, the forces F obtainable in the direction of the arrow 71 will be substantially as set forth in the following table.

TABLE OF FORCE IN GRAMS

| B (mm) | A = .01 mm C = (mm) | | | | | A = 1.0 mm C = (mm) | | | | |
|---|---|---|---|---|---|---|---|---|---|---|
| | 1.0 | 1.5 | 2.0 | 2.5 | 3.0 | 1.0 | 1.5 | 2.0 | 2.5 | 3.0 |
| 0.0 | 10 | 10 | 5 | 5 | 5 | 10 | 10 | 5 | 5 | 5 |
| 0.5 | 60 | 45 | 40 | 30 | 25 | 30 | 25 | 20 | 15 | 15 |
| 1.0 | 90 | 75 | 60 | 55 | 45 | 50 | 40 | 30 | 25 | 25 |
| 1.5 | 120 | 90 | 75 | 70 | 60 | 65 | 50 | 40 | 40 | 35 |
| 2.0 | 130 | 105 | 90 | 80 | 70 | 75 | 60 | 50 | 50 | 40 |
| 2.5 | 135 | 120 | 115 | 100 | 85 | 80 | 65 | 60 | 55 | 50 |
| 3.0 | 135 | 120 | 125 | 120 | 105 | 80 | 70 | 65 | 65 | 60 |
| 3.5 | 130 | 110 | 125 | 125 | 120 | 80 | 70 | 70 | 70 | 65 |
| 4.0 | 120 | 100 | 125 | 130 | 120 | 75 | 65 | 70 | 70 | 65 |
| 4.5 | — | 90 | 110 | 120 | 115 | — | 55 | 65 | 65 | 65 |
| 5.0 | — | — | 100 | 100 | 105 | — | — | 60 | 60 | 60 |
| 5.5 | — | — | — | 80 | 80 | — | — | — | 50 | 50 |
| 6.0 | — | — | — | — | 70 | — | — | — | — | 40 |

The above table indicates the various forces in grams that are obtainable with the various combinations of module spacing. For example, with A=0.01 mm, B=1.5 mm, and C=2.0 mm, a force of about 75 grams will be obtained. If dimensions B and C are kept the same, but A is increased to 1.0 mm, the force becomes 40 grams. Reading down the columns under a selected value for A and C will show the change in force as the module 60 translates and causes B to increase. Obviously, if the A, B and C parameters vary from those shown, other force values will be obtained. The tabulated values should be considered only as a general guide and will vary with changes in magnetic material, module dimensions and other well known factors.

Referring again to FIG. 10, it should be recognized that module 66 is repelling module 60 while module 65 is attracting module 60. Reversing the polarity of module 60, for example, will cause the force to reverse direction.

All of the examples discussed above have shown the modules applied buccally to the dental arches. However, the modules can be installed lingually either as an alternative or in combination with a buccal construction. Use of both locations in consort will provide increased force where desired.

An additional advantage derived from the sliding relationship of modules as exemplified in FIGS. 8 and 9 is the avoidance of interference with eccentric mandibular movement.

Figure 11:
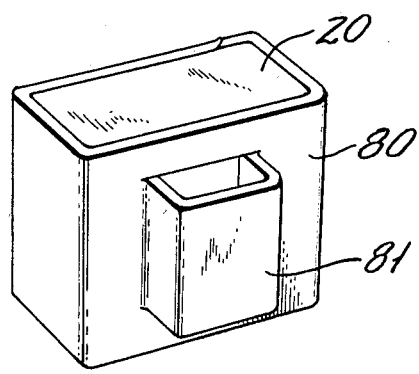
FIG. 11 is a view similar to FIG. 3 but showing a modification of the module construction.

The module shown and described with reference to FIG. 3 required welding the separate tunnel members 24 and 26 to the jacket 22. This construction can be simplified with a slight reduction in the front to back dimension of the module by resorting to the modification, presently preferred, and shown in FIG. 11. The magnetic body 20 covered with a bio-compatible coating can be the same as that in FIG. 3. However, the body 20 is now jacketed with the metal sleeve 80 from which the vertical and horizontal tunnels (only the vertical tunnel 81 being visible in FIG. 11) are produced by a stamping operation or the like prior to forming into a sleeve. Because the tunnels are shorter than the corresponding dimension of the sleeve 80, the horizontal tunnel is not visible, but it is similar to tunnel 81 except for being orthogonally related thereto. The thickness dimension of the module because of elimination of the extra metal parts will be thinner than the module of FIG. 3 by an amount equal to twice the thickness of the metal sheet. The sleeve 80, like sleeve 22, can be constructed of type 316L stainless steel.

Having described the presently preferred embodiments of the present invention it should be understood that various changes in construction can be introduced by those skilled in the subject art without departing from the true spirit of the invention as defined in the appended claims.

What is claimed is:

1. A universal kit for construction of magnetic force orthodontic appliances comprising in combination a plurality of modules each comprising a body of permanently magnetized material and means defining at least two orthogonally related through passages of non-circular cross-section, and a supply of attachment wire having a cross-section that permits threading said wire through either of said passages while precluding rotation of said module about said wire.

2. A universal kit according to claim 1, characterized in that said attachment wire consists of two lengths of edgewise wire bonded together side-by-side.

3. A universal kit according to claim 2, characterized in that said two lengths of edgewise wire are welded together in edge-to-edge relationship with the narrower sides in contact.

4. A universal kit according to claim 3, characterized in that the cross-sectional dimensions of each length of said attachment wire are about 0.022" by 0.056".

5. A universal kit according to claim 4, characterized in that each of said through passages has a rectangular cross-section of about 0.022" by 0.056".

6. A universal kit according to claim 5, characterized in that one of said two passages is disposed on one side of said module with its longitudinal axis oriented parallel to the axis of polarization of said body of magnetized material, and the other of said two passages is disposed on the opposite side of said module.

7. A universal kit according to claim 6, characterized in that said kit further comprises a set of gages for use in spacing said modules during installation within the oral cavity of a subject to develop a selected force consistent with a desired orthodontic procedure.

8. A universal kit according to claim 1, characterized in that one of said two passages is disposed on one side of said module with its longitudinal axis oriented parallel to the axis of polarization of said body of magnetized material, and the other of said two passages is disposed on the opposite side of said module.

9. A universal kit according to claim 8, characterized in that said kit further comprises a set of gages for use in spacing said modules during installation within the oral cavity of a subject to develop a selected force consistent with a desired orthodontic procedure.

10. A universal kit according to claim 1, characterized in that said kit further comprises a set of gages for use in spacing said modules during installation within the oral cavity of a subject to develop a selected force consistent with a desired orthodontic procedure.

11. A universal kit according to claim 1, characterized in that each said module comprises a parallelepiped shaped body of a magnetized material having an axis of magnetic polarization that extends between and normal to two opposing faces of said body, said body having bio-compatible surfaces, and a sleeve of bio-compatible stainless steel jacketing said body coaxially with said axis of magnetic polarization, said sleeve including said means defining said through passages.

12. A universal kit according to claim 11, characterized in that said means defining said through passages comprises for each passage a portion of said sleeve that has been displaced by stamping from the principal plane of a wall of said sleeve.

13. A universal kit according to claim 12, characterized in that said attachment wire consists of two lengths of edgewise wire bonded together side-by-side.

14. A universal kit according to claim 13, characterized in that said two lengths of edgewise wire are welded together in edge-to-edge relationship with the narrower sides in contact.

15. A universal kit according to claim 14, characterized in that the cross-sectional dimensions of each length of said attachment wire are about 0.022" by 0.056".

16. A universal kit according to claim 15, characterized in that each of said through passages has a rectangular cross-section of about 0.022" by 0.056".

17. A universal kit according to claim 16, characterized in that one of said two passages is disposed on one side of said module with its longitudinal axis oriented parallel to the axis of polarization of said body of magnetized material, and the other of said two passages is disposed on the opposite side of said module.

18. A universal kit according to claim 17, characterized in that said kit further comprises a set of gages for use in spacing said modules during installation within the oral cavity of a subject to develop a selected force consistent with a desired orthodontic procedure.

19. A universal kit according to claim 12, characterized in that said kit further comprises a set of gages for use in spacing said modules during installation within the oral cavity of a subject to develop a selected force consistent with a desired orthodontic procedure.

20. A module for use in construction of magnetic force orthodontic appliances in which the module is threaded on an attachment wire having a non-circular cross-section, said module comprising a body of permanently magnetized material and means defining at least two orthogonally related through passages of non-circular cross-section for receiving said attachment wire while precluding rotation of said module about said wire.

21. A module according to claim 20, characterized in that one of said two passages is oriented with its longitudinal axis parallel to the axis of polarization of said body of magnetized material on one side of said module, and the other of said two passages is on the other side of said module.

22. A module according to claim 21, characterized in that said module comprises a parallelepiped shaped body of a cobalt-rare earth magnetized material having said axis of magnetic polarization extending between and normal to two opposing faces of said body, said body being covered on all surfaces with a coating layer of a bio-compatible material, and a sleeve of bio-compatible stainless steel jacketing said coated body coaxially with said axis of magnetic polarization, said sleeve including said means defining said through passages.

* * * * *